(12) United States Patent
Bauer et al.

(10) Patent No.: US 11,433,052 B2
(45) Date of Patent: Sep. 6, 2022

(54) 5-LOX AND COX-2 INHIBITION FOR TREATMENT IN CONNECTION WITH BLOOD-BRAIN BARRIER DYSFUNCTION

(71) Applicant: University of Kentucky Research Foundation, Lexington, KY (US)

(72) Inventors: Bjoern Bauer, Lexington, KY (US); Anika Maria Sophie Hartz, Lexington, KY (US); Brent Scot Sokola, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/870,625

(22) Filed: May 8, 2020

(65) Prior Publication Data

US 2020/0352910 A1 Nov. 12, 2020

Related U.S. Application Data

(60) Provisional application No. 63/021,536, filed on May 7, 2020, provisional application No. 62/845,165, filed on May 8, 2019.

(51) Int. Cl.
| | |
|---|---|
| *A61K 31/415* | (2006.01) |
| *A61K 31/40* | (2006.01) |
| *A61K 31/381* | (2006.01) |
| *A61K 45/06* | (2006.01) |
| *A61P 25/08* | (2006.01) |
| *A61K 31/407* | (2006.01) |
| *A61K 31/22* | (2006.01) |

(52) U.S. Cl.
CPC ............ *A61K 31/415* (2013.01); *A61K 31/22* (2013.01); *A61K 31/381* (2013.01); *A61K 31/407* (2013.01); *A61K 45/06* (2013.01); *A61P 25/08* (2018.01)

(58) Field of Classification Search
CPC ..... A61K 31/415; A61K 31/40; A61K 31/381
USPC ........................................ 514/406, 413, 443
See application file for complete search history.

(56) References Cited

PUBLICATIONS

Bauer Lab Research, Epilepsy Research and Education Group, Jul. 8, 2020, pp. 1-10.
Bauer, Bjorn, Blood-brain barrier function in epilepsy: new targets for therapy?; Nov. 5, 2011, pp. 1-11.
Bauer, Bjorn, Targeting the LOX/COX dual pathway: blood-brain barrier repair in epilepsy; Mar. 30, 2012, pp. 1-33.
Bauer, Bjorn, Targeting the LOX/COX dual pathway: blood-brain barrier repair in epilepsy; Apr. 2, 2012, pp. 1-33.
Hartz, et al., Blood-brain barrier function in epilepsy; University of Minnisota, 2012; poster.
Bauer, Bjorn, The blood-brain barrier in epilepsy; Midwest Seizure Smart Summer Conference, Jul. 19, 2012, pp. 1-46.
Bauer, Bjorn, The blood-brain barrier in epilepsy; Neurology Grand rounds, Jul. 26, 2012, pp. 1-50.
Bauer, Bjorn, The blood-brain barrier in epilepsy; Faculty Meeting, Sep. 18, 2012, pp. 1-50.
Bauer, Bjorn, Blood-brain barrier function in epilepsy: new targets for therapy?; CVB 2013, pp. 1-33.
Bauer, Bjorn, Blood-brain barrier function in epilepsy: new targets for therapy; Upsher Smith Meeting, Jun. 27, 2013, pp. 1-29.
Bauer, Bjorn, Blood-brain barrier function in epilepsy: new targets for therapy?; West Virginia University, Aug. 5, 2013, pp. 1-49.
Bauer, Bjorn, Blood-brain barrier function in epilepsy: new targets for therapy?; University of Kentucky, Aug. 27, 2013, pp. 1-48.
Bauer, Bjorn, Blood-brain barrier function in epilepsy: new targets for therapy?; NCI, Frederick, Sep. 19, 2013, pp. 1-28.

*Primary Examiner* — Raymond J Henley, III
(74) *Attorney, Agent, or Firm* — Stites & Harbison, PLLC; Mandy Wilson Decker; Gary N. Stewart

(57) ABSTRACT

Methods of reducing blood brain barrier dysfunction involve inhibiting 5-LOX and COX-2.

24 Claims, 7 Drawing Sheets

5-LOX AND COX-2 INHIBITION FOR TREATMENT IN CONNECTION WITH BLOOD-BRAIN BARRIER DYSFUNCTION

RELATED APPLICATIONS

This application claims priority from U.S. Provisional Application Ser. No. 62/845,165, filed May 8, 2019, and 63/021,536, filed May 7, 2020, the entire disclosures of which are incorporated herein by this reference.

GOVERNMENT INTEREST

This invention was made with government support under grant number 1R01NS079507 awarded by the National Institutes of Health. The government has certain rights in the invention.

TECHNICAL FIELD

The presently-disclosed subject matter generally relates reduction in blood brain barrier (BBB) dysfunction, including reduction in brain capillary leakage and vascular inflammation. In particular, certain embodiments of the presently-disclosed subject matter relate to treatment to administering a composition to inhibit 5-LOX and COX-2 to reduce BBB dysfunction, having utility in the context of treating conditions such as seizure and epilepsy.

INTRODUCTION

Blood-brain barrier (BBB) dysfunction can result in connection with vessel deformation, vascular leakage, vascular inflammation, altered clearance, changes to tight junction proteins, changes to metabolic enzymes, changes to signaling molecules, changes in leukocyte recruitment, and transporter overexpression.

BBB dysfunction is associated with various conditions impacting the brain, such as epilepsy, seizure, Alzheimer's disease and/or dementias, Parkinson's disease, brain cancer, multiple sclerosis, stroke, brain trauma, infectious diseases of the brain, and peripheral inflammation or inflammation of the central nervous system (CNS).

BBB dysfunction is recognized, for example, as both a cause and consequence of seizures in epilepsy. Published findings show that a dysfunctional barrier contributes to seizure genesis and promotes epilepsy progression. Nevertheless, therapeutic options for restoring barrier function are currently not available. Indeed, there are not any currently-available treatments that targets the blood-brain barrier to repair barrier dysfunction to improve conditions and symptoms associated with conditions associated with BBB dysfunction, such as seizure control in subjects with epilepsy.

The current standard of care for treatment of epilepsy involves the use of pharmacotherapy with anti-seizure drugs (ASDs), which act inside the brain on neurons. However, about 30%-40% of patients do not respond to ASDs, and even in patients who respond to ASDs, there are often adverse effects.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods of reducing blood brain barrier dysfunction, reducing capillary leakage, and reducing vascular inflammation. The presently-disclosed subject matter further includes methods of treating a subject for blood-brain barrier (BBB) dysfunction. The presently-disclosed subject matter further includes methods of treating a subject displaying epileptogenesis.

The presently-disclosed subject matter includes a method of reducing brain capillary leakage, which involves administering an effective amount of a composition to inhibit 5-LOX and COX-2. In some embodiments, the composition includes a 5-LOX inhibitor and a COX-2 inhibitor. In some embodiments, the composition includes a dual 5-LOX/COX-2 inhibitor. In some embodiments, the composition to inhibit 5-LOX and COX-2 can further include a lipoxin A4 receptor (LXA4-R) agonist.

In some embodiments, the presently-disclosed subject matter includes a method for treating a subject for blood-brain barrier (BBB) dysfunction, which involves identifying the subject as having or being at risk of BBB dysfunction, and administering to the subject a composition as described herein.

In some embodiments, the presently-disclosed subject matter includes a method for treating a subject displaying epileptogenesis, comprising identifying the subject has displaying epileptogenesis, and administering to the subject a composition as disclosed herein. In some embodiments, the subject displays epileptogenesis following brain trauma or a central nervous system (CNS) condition.

In some embodiments, the methods disclosed herein further involve identifying the subject as having a need for controlling seizures. In some embodiments, the methods disclosed herein further involve administering an anti-seizure drug (ASD).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1A:
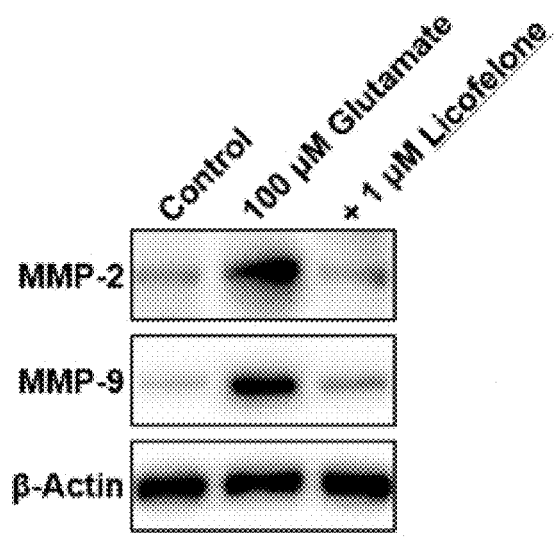
FIG. 1A includes Western blots showing MMP-2 and MMP-9 protein expression in isolated rat brain capillaries exposed to glutamate with or without a dual LOX/COX inhibitor.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods of reducing blood brain barrier dysfunction, reducing capillary leakage, and reducing vascular inflammation. The presently-disclosed subject matter further includes methods of treating a subject for blood-brain barrier (BBB) dysfunction. The presently-disclosed subject matter further includes methods of treating a subject displaying epileptogenesis.

The presently-disclosed subject matter includes a method of reducing brain capillary leakage, which involves administering an effective amount of a composition to inhibit 5-LOX and COX-2.

In some embodiments, the composition includes a 5-LOX inhibitor and a COX-2 inhibitor.

Various 5-LOX inhibitors are known to those skilled in the art and include, but are not limited to, zileuton, meclofenamate sodium, baicalein, caffeic acid, curcumin, hyperforin, and acetyl-keto-beta-boswellic acid (AKBA). Embodiments of the composition can include one or more 5-LOX inhibitors.

Various COX-2 inhibitors are also known to those skilled in the art and include, but are not limited to, celecoxib, valdecoxib, and rofecoxib. Embodiments of the composition can include one or more COX-2 inhibitors. Embodiments of the composition can include one or more COX-2 inhibitors and one or more 5-LOX inhibitors.

In some embodiments, the composition includes a dual 5-LOX/COX-2 inhibitor. Various dual 5-LOX/COX-2 inhibitors are known to those skilled in the art and include, but are not limited to licofelone, darbufelone, CI-987, and various thiazoles and thiazolidinones as disclosed, for example, in Liaras, et al., (2018) Molecules, 23(3): 685. Embodiments of the composition can include one or more dual 5-LOX/COX-2 inhibitors.

Embodiments of the composition can include one or more dual 5-LOX/COX-2 inhibitors and one or more COX-2 inhibitors. Embodiments of the composition can include one or more dual 5-LOX/COX-2 inhibitors and one or more 5-LOX inhibitors. Embodiments of the composition can include one or more dual 5-LOX/COX-2 inhibitors, one or more 5-LOX inhibitors, and one or more COX-2 inhibitors.

In some embodiments, the composition to inhibit 5-LOX and COX-2 can further include a lipoxin A4 receptor (LXA4-R) agonist. An exemplary LXA4 -R agonist that can be used in accordance with the presently-disclosed subject matter is BLM-111 ((5R,6R)-methyl 5,6,7-trihydroxyheptanoate).

Embodiments of the composition can include one or more LXA4-R agonists. Embodiments of the composition can include one or more LXA4-R agonists and one or more 5-LOX inhibitors. Embodiments of the composition can include one or more LXA4-R agonists and one or more COX-2 inhibitors. Embodiments of the composition can include one or more LXA4-R agonists and one or more dual 5-LOX/COX-2 inhibitors. Embodiments of the composition can include one or more LXA4-R agonists, one or more 5-LOX inhibitors, and one or more COX-2 inhibitors. Embodiments of the composition can include one or more LXA4-R agonists, one or more 5-LOX inhibitors, and one or more dual 5-LOX/COX-2 inhibitors. Embodiments of the composition can include one or more LXA4-R agonists, one or more COX-2 inhibitors, and one or more dual 5-LOX/COX-2 inhibitors.

In some embodiments, the presently-disclosed subject matter includes a method for treating a subject for blood-brain barrier (BBB) dysfunction, which involves identifying the subject as having or being at risk of BBB dysfunction, and administering to the subject a composition as described herein.

As will be recognized by those skilled in the art, BBB dysfunction is associated with one or more of vessel deformation, vascular leakage, vascular inflammation, altered clearance, changes to tight junction proteins, changes to metabolic enzymes, changes to signaling molecules, changes in leukocyte recruitment, and transporter overexpression. Examples of implicated transporters include, but are not limited to, P-glycoprotein (Pgp), Breast Cancer Resistance Protein (BCRP), Multidrug resistance-associated protein (MRP), Monocarboxylate transporter 1 (MCT1), L-Type Amino Acid Transporter 1 (LAT1), Organic anion-transporting polypeptide 2 (OATP2).

As will also be understood by those skilled in the art, BBB dysfunction is associated with various conditions impacting the brain, including, but not limited to seizure, epilepsy, Alzheimer's disease and/or dementias, Parkinson's disease, brain cancer, multiple sclerosis, stroke, brain trauma, an infectious disease of the brain, or peripheral inflammation or inflammation of the central nervous system (CNS). In this regard, treatment in accordance with the presently-disclosed subject matter can be useful in connection with a number of conditions.

In some embodiments, the presently-disclosed subject matter includes a method for treating a subject displaying epileptogenesis, comprising identifying the subject has displaying epileptogenesis, and administering to the subject a composition as disclosed herein. In some embodiments, the subject displays epileptogenesis following brain trauma or a central nervous system (CNS) condition. Examples of CNS conditions include, but are not limited to, stroke, multiple sclerosis, Alzheimer's disease, and Parkinson's disease.

In some embodiments, the methods disclosed herein further involve identifying the subject as having a need for controlling seizures.

In some embodiments, the methods disclosed herein further involve administering an anti-seizure drug (ASD).

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

With respect to the therapeutic methods of the presently disclosed subject matter, a preferred subject is a mammal. A preferred mammal is a human. As used herein, the term "subject" includes both human and animal subjects. Thus, veterinary therapeutic uses are provided in accordance with the presently disclosed subject matter.

As used herein, the terms "treatment" or "treating" relate to any therapeutic treatment and/or prophylactic treatment to prevent development or reduce severity of a condition. The terms "treatment" or "treating" include: preventing a condition; (2) inhibiting the conditions, i.e., arresting their development; or (3) ameliorating or relieving the symptoms of these conditions, i.e., causing regression of one or more of the conditions.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

The studies described in these Examples examined the effect of LOX inhibition and COX inhibition blood brain barrier leakage.

Figure 1B:
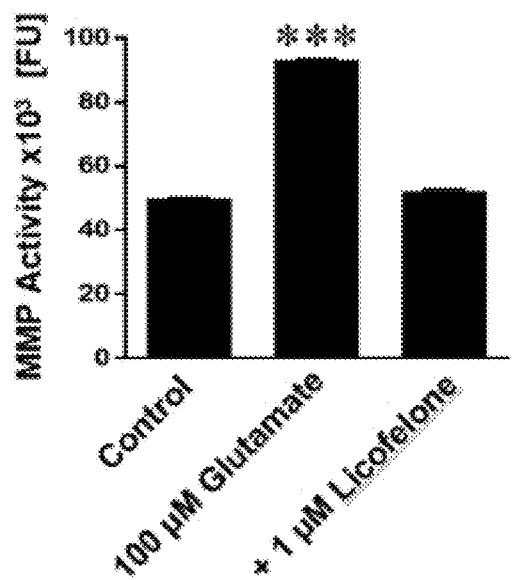
FIG. 1B includes a bar graph reporting MMP activity assessed in isolated capillaries exposed to glutamate with or without dual LOX/COX inhibitor.
Figure 1C:
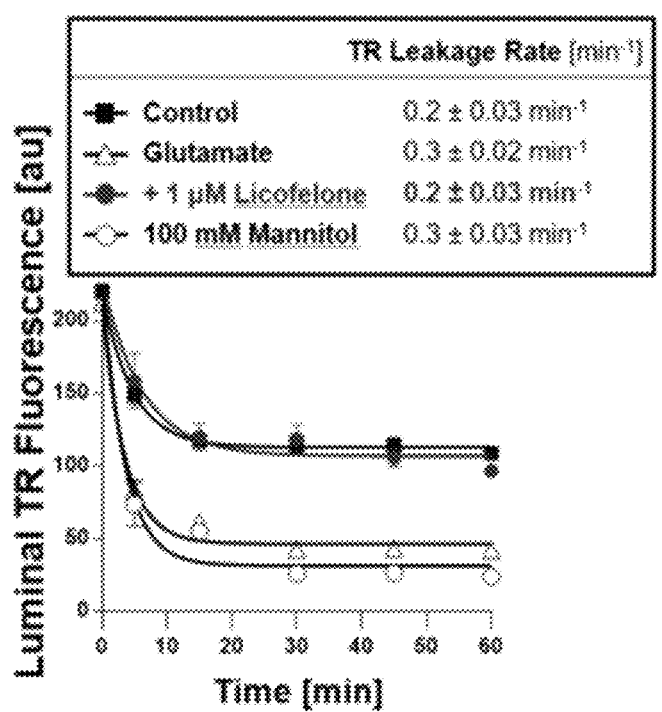
FIG. 1C includes the results of a Texas Red leakage assay showing glutamate-mediated barrier leakage with or without dual LOX/COX inhibitor.

With reference to FIGS. 1A-1C, the effect of dual LOX-COX inhibition on glutamate-mediated capillary leakage was tested. Isolated rat brain capillaries were exposed to 100 µM glutamate with or without 100 µM of the dual LOX/

COX inhibitor, licofelone (LCF). As the results reflect, dual LOX/COX inhibition with licofelone reduced glutamate-mediated capillary leakage.

FIG. 1A includes Western blots showing MMP-2 and MMP-9 protein expression in isolated rat brain capillaries exposed to 100 μM glutamate with or without LCF. β-Actin was used as protein loading control. While exposure to glutamate resulted in increased protein levels of MMP-2 and MMP-9, samples treated with LCF did not show increased protein levels.

FIG. 1B is a bar graph illustrating MMP activity assessed in isolated capillaries exposed to 100 μM glutamate with or without LCF. While exposure to glutamate resulted in increased MMP activity, samples treated with LCF did not show increased activity.

FIG. 1C includes the results of a Texas Red leakage assay showing glutamate-mediated barrier leakage reduction in samples with LCF. Data are 0-255 AFU and presented as mean±SEM for n=7 brain capillaries per time point from one capillary isolation with pooled tissue from n=10 rats. ***Significantly higher than control, $p<0.001$.

Figure 2A:
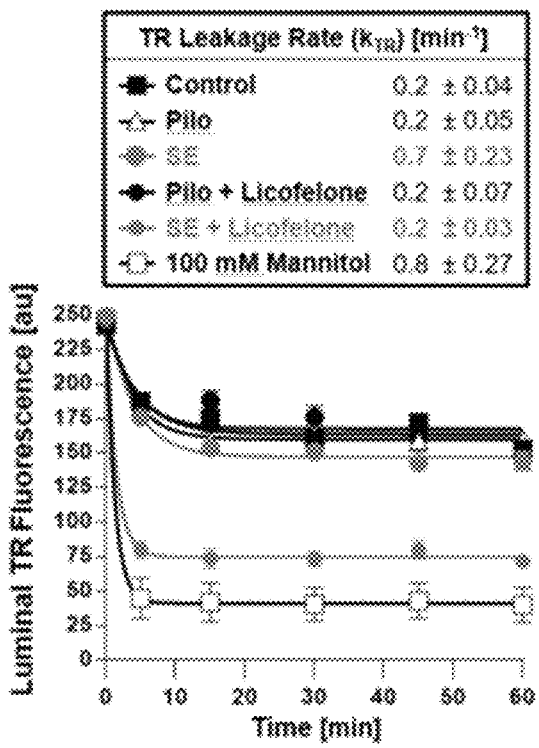
FIG. 2A includes the results of a Texas Red leakage assay showing seizure-mediated capillary leakage with or without dual LOX/COX inhibitor.
Figure 2B:
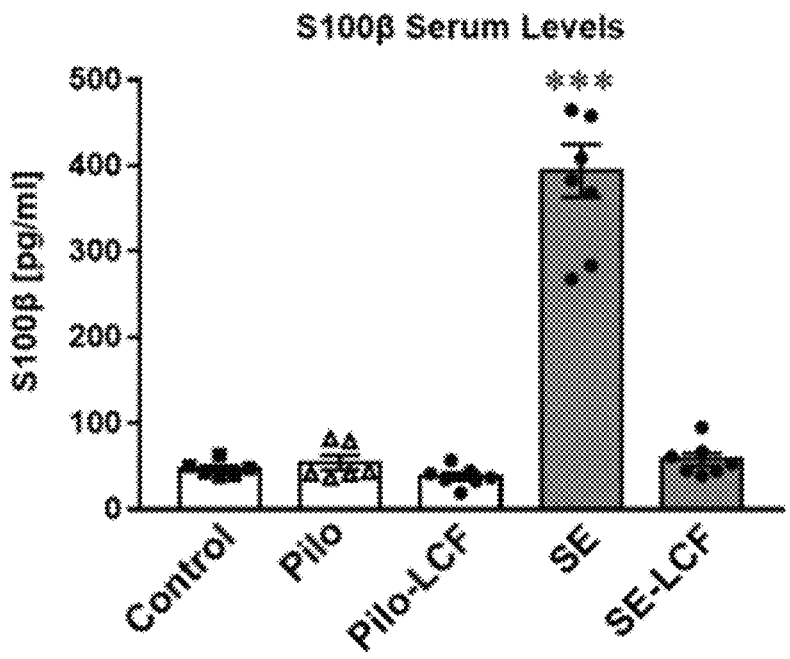
FIG. 2B includes a bar graph showing S100β levels in serum in from pilocarpine-induced status epilepticus (SE) animals compared to normal animals, with or without dual LOX/COX inhibitor.

With reference to FIGS. 2A and 2B, the effect of dual LOX-COX inhibition on seizure-mediated capillary leakage was tested. Rats were treated with 10 mg/kg LCF (i.p., 7 injections). Capillaries were isolated 2 d after status epilepticus (SE)-induction with pilocarpine.

Texas Red (TR) leakage from capillary lumens was monitored by confocal microscopy. Mannitol served as a positive control for barrier opening. (Hartz et al., 2012). Data includes mean±SEM (n=10 capillaries); arbitrary units (0-255). B) S100β ELISA (Millipore). Statistics: ***$p<0.001$ (ANOVA). With reference to FIG. 2A, these data indicate that LCF treatment prevents capillary leakage in SE rats.

Serum levels of S100β were assessed by ELISA (Millipore). Statistics: ***$p<0.001$ (ANOVA). Data: mean±SEM. With reference to FIG. 2B, these data indicate that LCF treatment reduces S100β levels in serum from SE rats.

Figure 3:
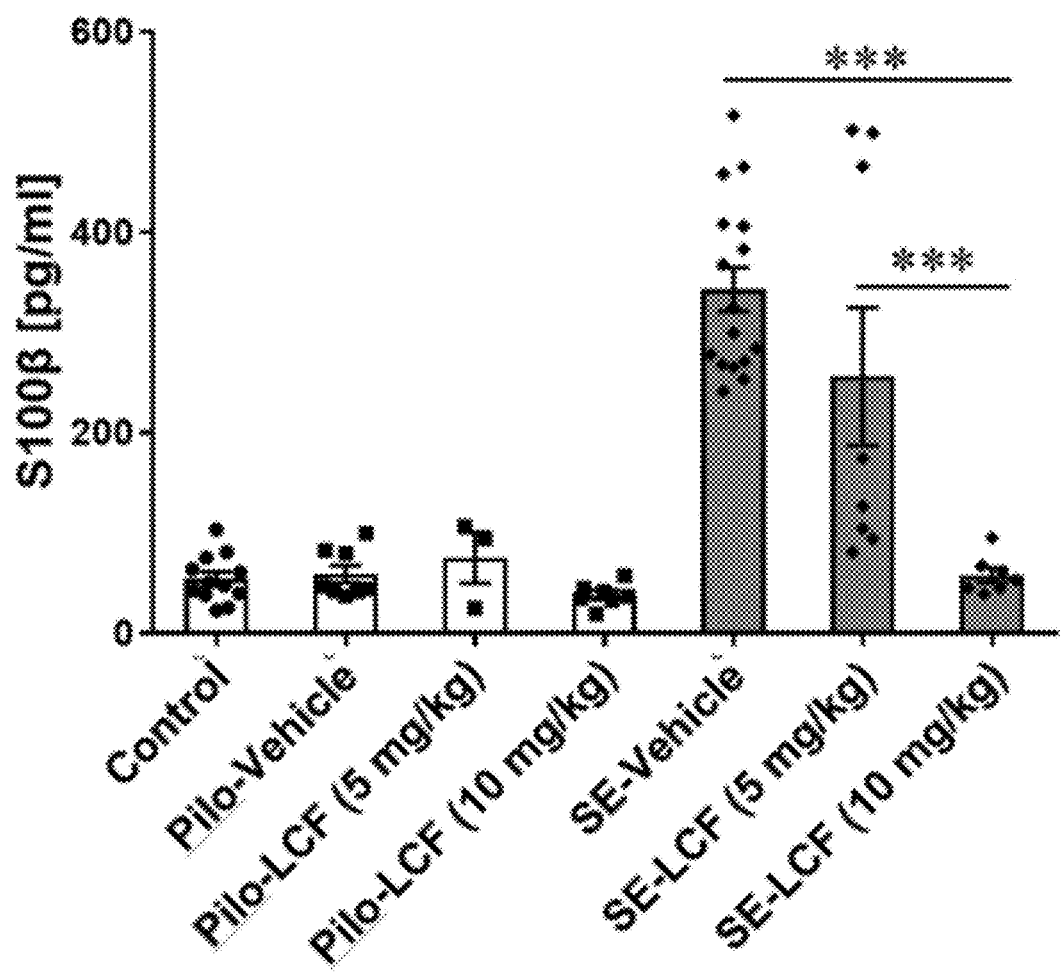
FIG. 3 includes a bar graph showing S100β levels in serum in from pilocarpine-induced status epilepticus (SE) animals compared to normal animals, with or without dual LOX/COX inhibitor, at different doses.

The effect of dual LOX-COX inhibition on seizure-mediated capillary leakage was further tested in rates treated with either 5 mg/kg or 10 mg/kg LCF (i.p., 7 injections). Capillaries were isolated 2 d after SE-induction with pilocarpine. Serum levels of S100β were assessed by ELISA (Millipore). With reference to FIG. 3, LCF treatment was found to inhibit capillary leakage in a dose-dependent manner, as reflected by S100β levels in serum from SE rats.

Figure 4A:
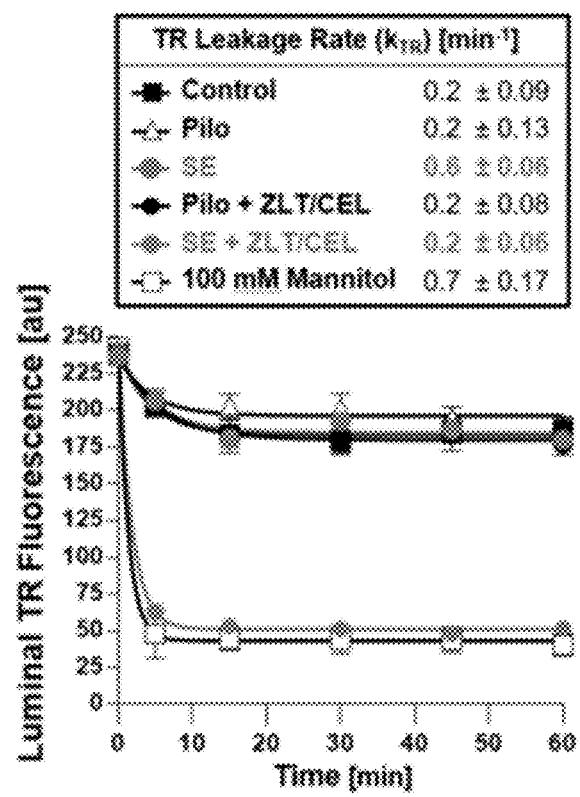
FIG. 4A includes the results of a Texas Red leakage assay showing seizure-mediated capillary leakage with or without a LOX inhibitor and a COX inhibitor.
Figure 4B:
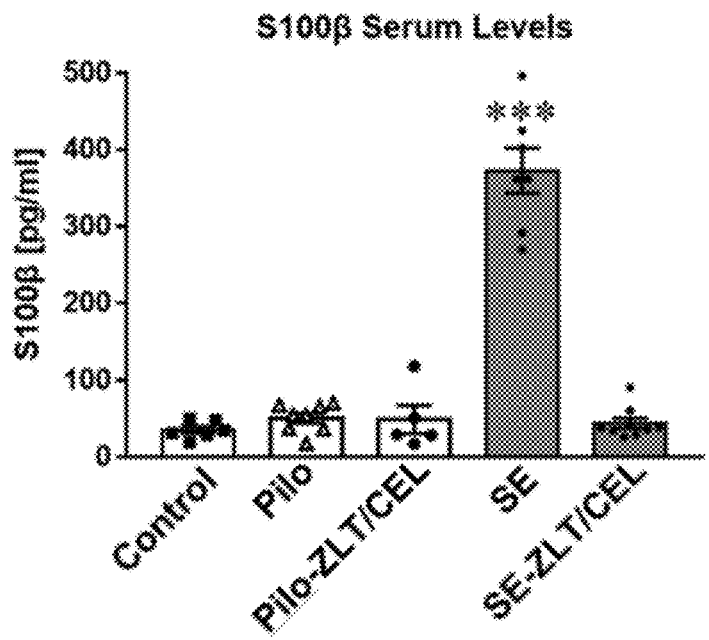
FIG. 4B includes a bar graph showing S100β levels in serum in from pilocarpine-induced status epilepticus (SE) animals compared to normal animals, with or without a LOX inhibitor and a COX inhibitor.

With reference to FIGS. 4A and 4B, the effect of a combination of a LOX inhibitor and a COX inhibitor on seizure-mediated capillary leakage was tested. Rats were treated with zileuton (ZLT) and celecoxib (CEL) (5 mg/kg and 10 mg/kg; i.p., 7 injections). Capillaries were isolated 2 d after SE-induction with pilocarpine.

Texas Red (TR) leakage from capillary lumens monitored by confocal microscopy (mannitol: positive control for barrier opening; Hartz et al., 2012). Data: mean±SEM (n=10 capillaries); arbitrary units (0-255). With reference to FIG. 4A, these data indicate that ZLT/CEL treatment prevents capillary leakage in SE rats.

Serum levels of S100β were assessed by ELISA (Millipore). Statistics: ***$p<0.001$ (ANOVA). Data: mean±SEM. With reference to FIG. 4B, these data indicate that ZLT/CEL treatment reduces S100β levels in serum from SE rats.

With reference to FIGS. 5A-5E, the effect of a combination of a LOX inhibitor, a COX inhibitor, and a LXA4-R agonist on seizure-mediated capillary leakage was tested. Twelve-month old chronic epileptic (CE) rats were treated with zileuton (ZLT)/celecoxib (CEL)/BML-111 (BML) (5/10/1 mg/kg; every 12 h for 10 days). As the data reflect, Targeting LOX/COX/LXA4-R Reduces Barrier Leakage and Vascular Inflammation in Chronic Epileptic (CE) Rats. Statistics: ***$p<0.001$ (ANOVA).

Figure 5A:
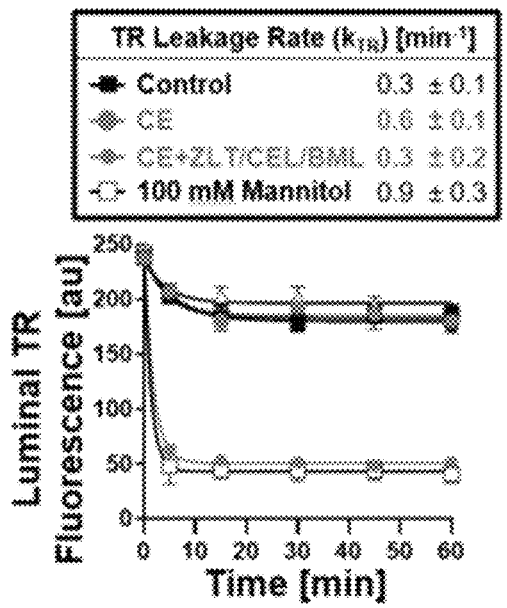
FIG. 5A the results of a Texas Red leakage assay showing capillary leakage in normal and chronic epileptic animals, with or without a LOX inhibitor, a COX inhibitor, and a LXA-R agonist.

Texas Red (TR) leakage from capillary lumens was monitored by confocal microscopy (mannitol: positive control for barrier opening; Hartz et al., 2012). Data: mean±SEM (n=10 capillaries); arbitrary units (0-255). Control: n=7; CE: n=3; CE+ZLT/CEL/BML: n=5. With reference to FIG. 5A, these data indicate that ZLT/CEL/BML treatment prevents capillary leakage in SE rats.

Figure 5B:
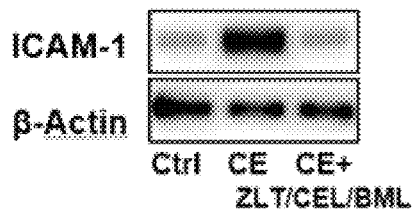
FIG. 5B includes Western blots showing ICAM-1 protein expression in isolated brain capillaries in normal and chronic epileptic animals, with or without a LOX inhibitor, a COX inhibitor, and a LXA-R agonist.
Figure 5C:
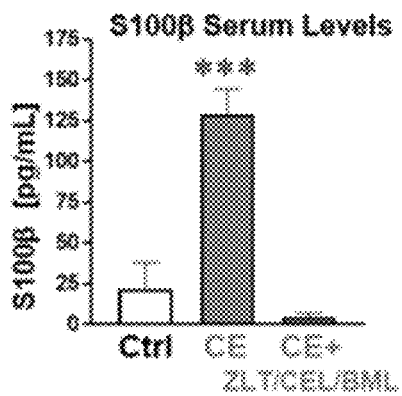
FIG. 5C includes a bar graph showing S100β levels in serum in from normal and chronic epileptic animals, with or without a LOX inhibitor, a COX inhibitor, and a LXA-R agonist.
Figure 5D:
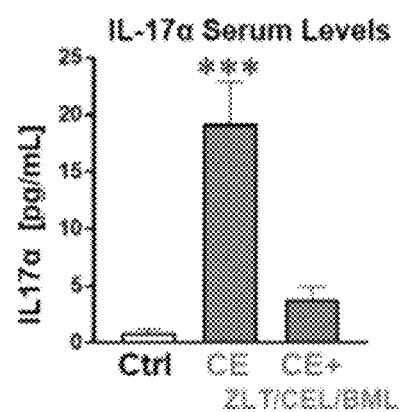
FIG. 5D includes a bar graph showing IL-17α levels in serum in from normal and chronic epileptic animals, with or without a LOX inhibitor, a COX inhibitor, and a LXA-R agonist.
Figure 5E:
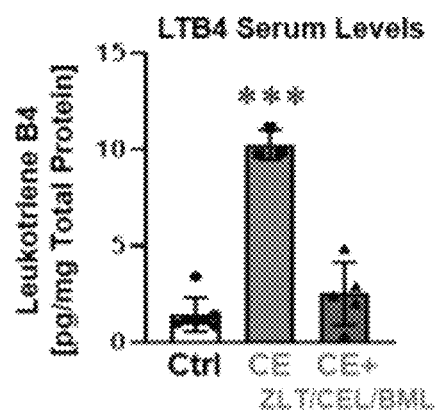
FIG. 5E includes a bar graph showing LTB4 levels in serum in from normal and chronic epileptic animals, with or without a LOX inhibitor, a COX inhibitor, and a LXA-R agonist.

FIG. 5B includes Western blots showing ICAM-1 protein expression in chronic epileptic rat brain capillaries with or without ZLT/CEL/BML. β-Actin was used as protein loading control. While exposure there were increased protein levels of ICAM-1 in the chronic epileptic rats, rats treated with ZLT/CEL/BML did not show increased protein levels.

Serum levels of S100β were assessed by ELISA (Millipore). With reference to FIG. C, these data indicate that ZLT/CEL/BML treatment reduces S100β levels in serum from chronic epileptic rats.

Serum levels of IL-17α were assessed by ELISA (Millipore). With reference to FIG. D, these data indicate that ZLT/CEL/BML treatment reduces IL-17α levels in serum from chronic epileptic rats.

Serum levels of LTB4 were assessed by ELISA (Millipore). With reference to FIG. D, these data indicate that ZLT/CEL/BML treatment reduces LTB4 levels in serum from chronic epileptic rats.

All publications, patents, and patent applications mentioned in this specification, and the applications to which priority is claimed, are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of reducing brain capillary leakage, comprising: identifying a subject having seizure, epilepsy, Alzheimer's disease and/or dementias, Parkinson's disease, brain cancer, multiple sclerosis, stroke, brain trauma, an infectious disease of the brain, and/or peripheral inflammation or inflammation of the central nervous system (CNS), and administering to the subject an effective amount of a composition to inhibit 5-LOX and COX-2 to reduce brain capillary leakage.

2. The method of claim 1, wherein the composition comprises a 5-LOX inhibitor and a COX-2 inhibitor.

3. The method of claim 2, wherein the 5-LOX inhibitor is zileuton.

4. The method of claim 2, wherein the COX-2 inhibitor is celecoxib.

5. The method of claim 2, wherein the 5-LOX inhibitor is zileuton and the COX-2 inhibitor is celecoxib.

6. The method of claim 1, wherein the composition comprises a dual 5-LOX/COX-2 inhibitor.

7. The method of claim 6, wherein the dual 5-LOX/COX-2 inhibitor is licofelone.

8. The method of claim 1, and further including a lipoxin A4 receptor (LXA4-R) agonist.

9. The method of claim 8, wherein the LXA4-R agonist is BLM-111 ((5R,6R)-methyl 5,6,7-trihydroxyheptanoate).

10. The method of claim 1, and further comprising administering an anti-seizure drug (ASD).

11. A method of reducing brain capillary leakage, for treating a subject for blood-brain barrier (BBB) dysfunction, comprising identifying the subject as having or being at risk of BBB dysfunction, and administering to the subject an effective amount of a composition to inhibit 5-LOX and COX-2.

12. The method of claim 11, wherein the subject has or is at risk of having seizure, epilepsy, Alzheimer's disease and/or dementias, Parkinson's disease, brain cancer, multiple sclerosis, stroke, brain trauma, an infectious disease of the brain, or peripheral inflammation or inflammation of the central nervous system (CNS).

13. A method of reducing brain capillary leakage, for treating a subject displaying epileptogenesis, comprising identifying the subject has displaying epileptogenesis, and administering to the subject the composition an effective amount of a composition to inhibit 5-LOX and COX-2.

14. The method of claim 13, and further comprising identifying the subject as having a need for controlling seizures.

15. The method of claim 13, wherein the epileptogenesis the subject displays epileptogenesis following brain trauma or a central nervous system (CNS) condition.

16. The method of claim 11 or 13, wherein the composition comprises a 5-LOX inhibitor and a COX-2 inhibitor.

17. The method of claim 16, wherein the 5-LOX inhibitor is zileuton.

18. The method of claim 16, wherein the COX-2 inhibitor is celecoxib.

19. The method of claim 16, wherein the 5-LOX inhibitor is zileuton and the COX-2 inhibitor is celecoxib.

20. The method of claim 11 or 13, wherein the composition comprises a dual 5-LOX/COX-2 inhibitor.

21. The method of claim 20, wherein the dual 5-LOX/COX-2 inhibitor is licofelone.

22. The method of claim 11 or 13, and further including a lipoxin A4 (LXA4) agonist.

23. The composition of claim 22, wherein the LXA4 agonist is BLM-111 ((5R,6R)-methyl 5,6,7-trihydroxyheptanoate).

24. The method of claim 11 or 13, and further comprising administering an anti-seizure drug (ASD).

* * * * *